Figure 1:
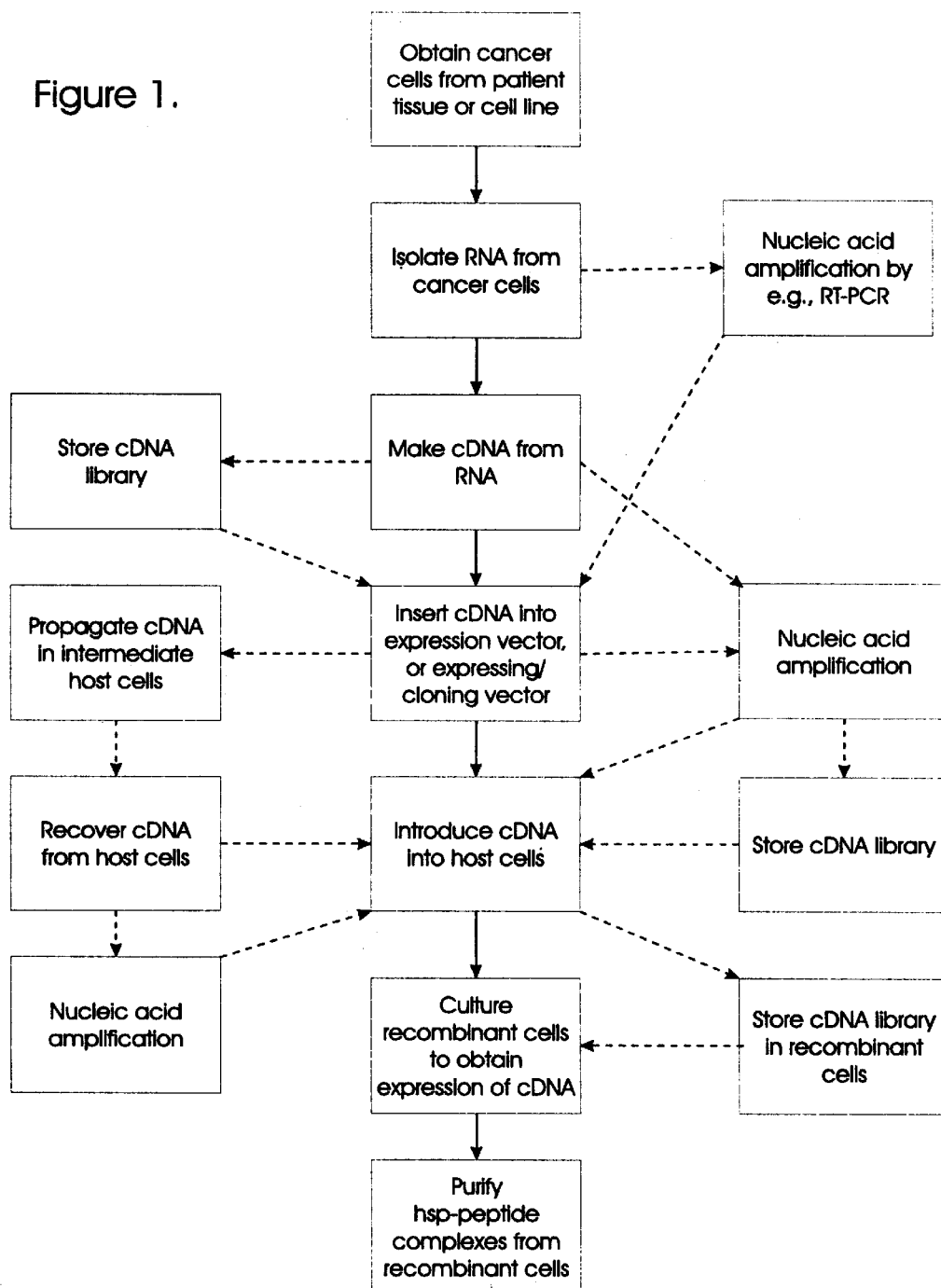

United States Patent [19]

Srivastava

[11] Patent Number: 5,948,646
[45] Date of Patent: Sep. 7, 1999

[54] METHODS FOR PREPARATION OF VACCINES AGAINST CANCER COMPRISING HEAT SHOCK PROTEIN-PEPTIDE COMPLEXES

[75] Inventor: Pramod K. Srivastava, Avon, Conn.

[73] Assignee: Fordham University, Bronx, N.Y.

[21] Appl. No.: 08/988,878

[22] Filed: Dec. 11, 1997

[51] Int. Cl.$^6$ .............................. C12P 21/06; C12N 15/00
[52] U.S. Cl. .................... 435/69.3; 530/403; 536/23.1; 536/23.4; 536/23.5; 435/320.1; 435/325
[58] Field of Search ................................ 435/69.3, 320.1, 435/325, 254.21, 235.1; 536/23.5, 23.4, 23.1; 530/403

[56] References Cited

U.S. PATENT DOCUMENTS

| | | |
|---|---|---|
| 4,690,915 | 9/1987 | Rosenberg . |
| 5,188,964 | 2/1993 | McGuire et al. . |
| 5,232,833 | 8/1993 | Sanders et al. . |
| 5,348,945 | 9/1994 | Berberian et al. . |
| 5,747,332 | 5/1998 | Wallen et al. . |
| 5,750,119 | 5/1998 | Srivastava et al. . |
| 5,830,464 | 2/1997 | Srivastava et al. . |
| 5,837,251 | 11/1998 | Srivastava . |

FOREIGN PATENT DOCUMENTS

| | | |
|---|---|---|
| 196 02 985 A1 | 7/1997 | Germany . |
| 2 251 186 | 7/1992 | United Kingdom . |
| WO 89/12455 | 12/1989 | WIPO . |
| WO 90/02564 | 3/1990 | WIPO . |
| WO 91/02077 | 2/1991 | WIPO . |
| WO 91/15572 | 10/1991 | WIPO . |
| WO 92/01717 | 2/1992 | WIPO . |
| WO 92/08484 | 5/1992 | WIPO . |
| WO 92/08488 | 5/1992 | WIPO . |
| WO 93/14118 | 7/1993 | WIPO . |
| WO 93/17712 | 9/1993 | WIPO . |
| WO 93/18146 | 9/1993 | WIPO . |
| WO 93/18147 | 9/1993 | WIPO . |
| WO 93/21529 | 10/1993 | WIPO . |
| WO 94/03208 | 2/1994 | WIPO . |
| WO 94/03599 | 2/1994 | WIPO . |
| WO 94/04676 | 3/1994 | WIPO . |
| WO 94/11513 | 5/1994 | WIPO . |
| WO 95/04824 | 2/1995 | WIPO . |
| WO 95/24923 | 9/1995 | WIPO . |
| WO 96/10411 | 4/1996 | WIPO . |
| WO 96/31613 | 10/1996 | WIPO . |
| WO 97/06685 | 2/1997 | WIPO . |
| WO 97/06821 | 2/1997 | WIPO . |
| WO 97/06828 | 2/1997 | WIPO . |
| WO 97/10000 | 3/1997 | WIPO . |
| WO 97/10001 | 3/1997 | WIPO . |
| WO 97/10002 | 3/1997 | WIPO . |
| WO 97/26910 | 7/1997 | WIPO . |

OTHER PUBLICATIONS

Ausubel et al., ed., 1988, *Current Protocols in Molecular Biology* (Greene Publish. Assoc. and Wiley Interscience) Chapter 13.

Barrios et al., "Mycobacterial heat–shock proteins as carrier molecules. II: The use of the 70–kDa mycobacterial heat–shock protein as carrier for conjugated vaccines that can circumvent the need for adjuvants and Bacillus Calmette Guérin priming", 1992, Eur. J. Immunol. 22:1365–1372.

Barrios et al., 1994, "Specificity of antibodies induced after immunization of mice with the mycobacterial heat shock proteins of 65 kD", Clin. Exp. Immunol. 98:224–228.

Barrios et al., 1994, "Heat shock proteins as carrier molecules: in vivo helper effect mediated by *Escherichia coli* GroEL and DnaK proteins requires cross–linking with antigen", Clin. Exp. Immunol. 98:229–233.

Belyavsky et al., 1989, "PCR–based cDNA libraries at the level of a few cells" Nucl. Acids. Res. 17:2919–2932.

Berger et al., 1992, "Guide to molecular cloning techniques", Methods in Enzymol. 152:307–389.

Blachere et al., 1993, "Immunization with GP96 heat shock proteins isolated from tumors or influenza virus infected cells elicits MHC–restricted, antigen–specific cytotoxic T lymphocytes against the corresponding cells/antigens" J. Cell. Biochem. 17D:124.

Blachere et al., 1993, "Heat Shock Protein Vaccines Against Cancer," J. Immunotherapy 14:352–356.

Choulika et al., 1996, "Transfer of a single gene containing long terminal repeats into the genome of mammalian cells by a retroviral vector carrying the cre gene and the loxP site" J. Virol. 70:1792–1798.

Craig, 1993, "Chaperones: Helpers Along the Pathways to Protein Folding" Science 260:1902–1904.

Domec et al., 1990, "cDNA library construction form small amounts of unfractionated RNA: association of cDNA synthesis with polymerase chain reaction amplification", Anal. Biochem. 188:422–426.

Ebert, 1987"Characterization of an immunosuppressive factor derived from colon cancer cells", J. Immunol. 138:2161–2168.

Falk et al., 1990, "Cellular Peptide Composition Governed by Major Histocompatibility Complex Class I Molecules", Nature 348:248–251.

(List continued on next page.)

Primary Examiner—Paula K. Hutzell
Assistant Examiner—Geetha P. Bansal
Attorney, Agent, or Firm—Pennie & Edmonds LLP

[57] ABSTRACT

The present invention relates to methods for preparing immunogenic, prophylactically and therapeutically effective complexes of heat shock proteins noncovalently associated with antigenic peptides of cancer cells. The claimed methods comprise the constructing of a cDNA library from cancer or preneoplastic cell RNA, expressing the cDNA library in an appropriate host cell, and recovering the immunogenic complexes from the cells. Large amounts of such immunogenic complexes can be obtained by large-scale culturing of host cells containing the cDNA library. The complexes can be used as a vaccine to elicit specific immune responses against cancer or preneoplastic cells, and to treat or prevent cancer.

39 Claims, 1 Drawing Sheet

OTHER PUBLICATIONS

Falk et al., "Allele–specific Motifs Revealed by Sequencing of Self–peptides Eluted from MHC Molecules" 1991, Nature 351:290–296.

Feldweg et al., "Evidence for biochemical Heterogeneity of gp96 heat shock protein/tumor rejection antigen" 1993, J. Cell. Biochem. Suppl. 17D:108.

Flynn et al., 1991, "Peptide–binding Specificity of the Molecular Chaperone BiP" Nature 353:726–730.

Flynn et al., 1989, "Peptide binding and release by proteins implicated as catalysis of protein assembly" Science 245:385–390.

Franklin, 1993, "Making vaccines fit the Cancer" New Scientist 140:17.

Gething, 1992, "Protein Folding in the Cell" Nature 355:33–45.

Gorman, 1990, "Mammalian Cell Expression", Curr. Opin. Biotechnol. 1:36–47.

Heike et al., 1994, "Protective Cellular Immunity against a Spontaneous Mammary Carcinoma from ras Transgenic Mice", Immunobiology 190:411–423.

Huynh et al., 1984, *DNA Cloning Techniques vol. I: A Practical Approach* (IRL Press, Oxford) pp. 49–78.

Jakob et al., "Small Heat Shock Proteins Are Molecular Chaperones" 1993, J. Biol. Chem. 268:1517–1520.

Jardetzky et al., 1991, "Identification of Self Peptides Bound to Purified HLA–B27" Nature 353:326–329.

Lakey et al., 1987, "Identification of a peptide binding protein that plays a role in antigen presentation" Proc. Natl. Acad. Sci. USA 84:1659–1663.

Lanzavecchia, 1993, "Identifying Strategies for Immune Intervention" Science 260:937–944.

Levinson et al., 1979, "Metal Binding Drugs Induce Synthesis of Four Proteins in Normal Cells" Biol. Trace Element Res. 1:15–23.

Levy, 1991, "ATP is Required for In Vitro Assembly of MHC Class I Antigens but Not for Transfer of Peptides across the ER Membrane" Cell 67:265–274.

Li et al., 1993, "Tumor rejection antigen gp96/grp94 is an ATPase: Implications for protein folding and antigen presentation" Embo J. 12:3143–3151.

Linquist et al., 1988, "The heat–shock proteins" Ann. Rev. Genet. 22:631–677.

Luescher et al., 1991 "Specific Binding of Antigenic Peptides to Cell–associated MHC Class I Molecules", Nature 351:72–77.

Lukacs et al., 1993,"Tumor cells transfected with a bacterial heat–shock gene loss tumorigenicity and induce protein against tumors" J. Exp. Med. 178:343–348.

Lussow et al., 1991 "Mycobacterial heat–shock proteins as carrier molecules", Eur. J. Immunol. 21:2297–2302.

Madden et al., 1991 "The Structure of HLA–B27 Reveals Nonamer Self–peptides Bound in an Extended Conformation", Nature 353:321–325.

Maki et al., 1993,"Mapping of the Genes for Human Endoplasmic Reticular Heat Shock Protein gp96/grp94" Somatic Cell Mol. Genetics 19:73–81.

Maki et al., 1990, "Human homologue of murine tumor rejection antigen gp96: 5'–Regulatory and coding regions and relationship to stress–induced proteins" Proc. Natl. Acad. Sci. USA 87:5658–5663.

Makrides, 1996, "Strategies for achieving high level expression of genes in *Escherichia coli*" Microbiol. Rev. 60:512–538.

Mizoguchi et al., 1982, "Alterations in signal transduction molecules in T lymphocytes from Tumor–bearing mice", Science 258:1795–1798.

Palladino et al., 1987 "Expression of shared tumor–specific antigen by two chemically induced BALB/c sarcomas", Cancer Res. 47:5074–5079.

Prehn et al., 1957, "Immunity to methylcholanthrene–induced sarcomas" J. Cancer Inst. 18:769–778.

Rothman, 1989 "Polypeptide Chain Binding Proteins: Catalysts of Protein Folding and Related Processes in Cells", Cell 59:591–601.

Rotzschke et al., 1990, "Isolation and Analysis of Naturally Processed Viral Peptides as Recognized by Cytotoxic T cells" Nature 348:248–251.

Rudensky et al., 1991, "Sequence analysis of peptides bound to MHC class II molecules", Nature 353:622–627.

Salk et al., 1993, "A Strategy for Prophylactic Vaccination Against HIV" Science 260:1270–1272.

Sambrook et al., in *Molecular Cloning: A Laboratory Manual,* 2$^{nd}$ Ed., Chapter 8.

Schumacher et al., 1991 "Peptide Selection by MHC Class I Molecules", Nature 350:703–706.

Srivastava et al., 1993,"Peptide–Binding Heat Shock Proteins in the Endoplasmic Reticulum: Role in Immune Response to Cancer and in Antigen Presentation" Adv. Cancer Res. 62:153–177.

Srivastava et al., 1991, "Stress–induced proteins in immune response to cancer", Curr. Top. Microbiol. Immunol. 167:109–123.

Srivastava et al., 1994"Heat shock proteins transfer peptides during antigen processing and CTL priming", Immunogenetics 39:93–98.

Srivastava et al., 1989,"Identification of a Human Homologue of the Murine Tumor Rejection Antigen GP96," Cancer Res. 49:1341–1343.

Srivastava et al., 1993, "Evidence for peptide–chaperoning by the endoplasmic reticular heat shock protein GP96: Implications for vaccination against cancer and infectious diseases" J. Cell. Biochem. Supp. 17D:94 (Abstract NZ 014).

Srivastava et al., 1987 "5'–Structural analysis of genes encoding polymorphic antigens of chemically induced tumors", Proc. Natl. Acad. Sci. USA 84:3807–3811.

Srivastava et al., 1988, "Chromosomal Assignment of the Gene Encoding the Mouse Tumor Rejection Antigen gp96" Immunogenetics 28:205–207.

Srivastava et al., 1986 "Tumor rejection antigens of chemically induced sarcomas of inbred mice", Proc. Natl. Acad. Sci. USA 83:3407–3411.

Srivastava et al., 1984 "The Serologically Unique Cell Surface Antigen of Zajdela Ascitic Hepatoma is also its Tumor–Associated Transplantation Antigen", Int. J. Cancer 33:417–422.

Srivastava, 1991,"Protein Tumor Antigens", Curr. Opin. Immunol. 3:654–658.

Srivastava et al., 1988, "Individually distinct transplantation antigens of chemically induced mouse tumors" Immunol. Today 9:78–83.

Subbarao et al., 1992,"A General Overview of Viral Vaccine Development," Genetically Engineered Vaccines 327:51–57.

Suto et al., 1995,"A Mechanism for the Specific Immunogenicity of Heat Shock Protein–Chaperoned Peptides", Science 269:1585–1588.

Udono et al., 1993, "Heat Shock Protein 70–associated Peptides Elicit Specific Cancer Immunity" J. Exp. Med. 178:1391–1396.

Udono et al., 1993 "Comparison of Tumor–Specific Immunogenicities of Stress–Induced Proteins gp96, hsp90, and hsp70", J. Immunol. 152:5398–5403.

Udono et al., 1994, "Cellular requirements for tumor–specific immunity elicited by heat shock proteins:tumor rejection antigen gp96 primes CD8+ T cells in vivo", Proc. Natl. Acad. Sci. USA 91:3077–3081.

Udono, 1993, "Heat shock proteins HSP70, HSP90 and GP96 elicit tumor specific immunity to the tumors from which they are isolated" J. Cell. Biochem. Suppl. 17D:113 (Abstract NZ225).

Ullrich et al., 1986,"A mouse tumor–specific transplantation antigen is a heat shock–related protein" Proc. Natl. Acad. Sci. USA 83:3121–3125.

Van den Enyde et al., 1991, "The gene coding for a major tumor rejection antigen of tumor P815 is identical to the normal gene of syngeneic DBA/2 mice", J. Exp. Med. 173:1373–1384.

Vanbuskirk et al., 1989 "Peptide binding protein having a role in antigen presentation is a member of the hsp70 heat shock family", J. Exp. Med. 170:1799–1809.

Viitanen et al., 1992, "Mammalian mitochondrial chaperonin 60 functions as a single toroidal ring", J. Biol. Chem. 267:695–698.

Welch et al., 1985, "Rapid Purification of Mammalian 70,000–Dalton Stress Proteins: Affinity of the Proteins for Nucleotides" Mol. Cell. Biol. 5:1229–1237.

Welch et al., 1985, "Morphological study of the mammalian stress response: characterization of changes in cytoplasmic organelles, cytoskeleton, nucleoli, and appearance of intranuclear actin filaments in rat fibroblast after heat shock treatment", J. Cell. Biol. 101:1198–1211.

Welch et al., 1982, "Purification of the Major Mammalian Heat Shock Proteins" J. Biol. Chem. 357:14944–14959.

Welch, 1993, "How Cells Respond to Stress" Scientific American pp. 56–64.

Young, 1990,"Stress Proteins and Immunology" Annu. Rev. Immunol. 8:401–420.

METHODS FOR PREPARATION OF VACCINES AGAINST CANCER COMPRISING HEAT SHOCK PROTEIN-PEPTIDE COMPLEXES

This invention was made with government support under grant number CA44786 awarded by the National Institutes of Health, and grant number N652369715812 awarded by the United States Navy. The government has certain rights in the invention.

1. INTRODUCTION

The present invention relates to methods for preparing large amounts of immunogenic material that is useful as a vaccine for the prevention and/or treatment of cancer. The vaccine is comprised of noncovalent complexes of heat shock proteins (hsp), including, but not limited to, hsp70, hsp90, gp96, and protein disulfide isomerase, and antigenic peptides. The vaccine is capable of eliciting or augmenting a subject's immune response against a particular cancer.

2. BACKGROUND OF THE INVENTION

2.1. Pathobiology of Cancer

Cancer is characterized primarily by an increase in the number of abnormal cells derived from a given normal tissue. The disease process also involves invasion of adjacent tissues by these abnormal cells, and spread of these abnormal cells to regional lymph nodes and to distant sites (metastasis) via the circulatory system. Clinical data and molecular biologic studies indicate that cancer is a multistep process that begins with minor preneoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, Basic Pathology, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, I., Brostoff, J. and Male, D., 1993, Immunology, 3rd ed., Mosby, St. Louis, pps. 17.1–17.12).

2.2. Vaccination

Vaccination has eradicated certain diseases such as polio, tetanus, chicken pox, measles, etc. in many countries of the world. This approach has exploited the ability of the immune system to prevent infectious diseases. Such vaccination with non-live materials such as proteins generally leads to an antibody response or CD4+ helper T cell response (Raychaudhuri & Morrow, 1993, Immunology Today, 14:344–348). On the other hand, vaccination or infection with live materials such as live cells or infectious viruses generally leads to a CD8+ cytotoxic T-lymphocyte (CTL) response. A CTL response is crucial for protection against cancers, infectious viruses and bacteria. This poses a practical problem, for, the only way to achieve a CTL response is to use live agents which are themselves pathogenic. The problem is generally circumvented by using attenuated viral and bacterial strains, or by killing whole cells which can be used for vaccination. These strategies have worked well but the use of attenuated strains always carries the risk that the attenuated agent may recombine genetically with host DNA and turn into a virulent strain. Thus, there is need for methods which can lead to CD8+ CTL response by vaccination with non-live materials such as proteins in a specific manner.

The era of tumor immunology began with experiments by Prehn and Main, who showed that antigens on the methylcholanthrene (MCA)-induced sarcomas were tumor specific in that transplantation assays could not detect these antigens in normal tissue of the mice (Prehri et al., 1957, J. Natl. Cancer Inst. 18:769–778). This notion was confirmed by further experiments demonstrating that tumor specific resistance against MCA-induced tumors can be elicited in the mouse in which the tumor originated (Klein et al., 1960, Cancer Res. 20:1561–1572).

In subsequent studies, tumor specific antigens were also found on tumors induced with other chemical or physical carcinogens or on spontaneous tumors (Kripke, 1974, J. Natl. Cancer Inst. 53:1333–1336; Vaage, 1968, Cancer Res. 28:2477–2483; Carswell et al., 1970, J. Natl. Cancer Inst. 44:1281–1288). Since these studies used protective immunity against the growth of transplanted tumors as the criterion for tumor specific antigens, these antigens are also commonly referred to as "tumor specific transplantation antigens" or "tumor specific rejection antigens." Several factors can greatly influence the immunogenicity of the tumor, including, for example, the specific type of carcinogen involved, immunocompetence of the host and latency period (Old et al., 1962, Ann. N.Y. Acad. Sci. 101:80–106; Bartlett, 1972, J. Natl. Cancer Inst. 49:493–504).

Most, if not all, carcinogens are mutagens which may cause mutation, leading to the expression of tumor specific antigens (Ames, 1979, Science 204:587–593; Weisburger et al., 1981, Science 214:401–407). Some carcinogens are immunosuppressive (Malmgren et al., 1952, Proc. Soc. Exp. Biol. Med. 79:484–488). Experimental evidence suggests that there is a constant inverse correlation between immunogenicity of a tumor and latency period (time between exposure to carcinogen and tumor appearance) (Old et al., 1962, Ann. N.Y. Acad. Sci. 101:80–106; and Bartlett, 1972, J. Natl. Cancer Inst. 49:493–504). Other studies have revealed the existence of tumor specific antigens that do not lead to rejection, but, nevertheless, can potentially stimulate specific immune responses (Roitt, I., Brostoff, J. and Male, D., 1993, Immunology, 3rd ed., Mosby, St. Louis, pp. 17.1–17.12).

2.3. Heat Shock Proteins

Heat shock proteins (hsps) are also referred to interchangeably as stress proteins. The first stress proteins to be identified were proteins synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including nutrient deprivation, metabolic disruption, oxygen radicals, and infection with intracellular pathogens. (See Welch, May 1993, Scientific American 56–64; Young, 1990, Annu. Rev. Immunol. 8:401–420; Craig, 1993, Science 260:1902–1903; Gething et al., 1992, Nature 355:33–45; and Lindquist et al., 1988, Annu. Rev. Genetics 22:631–677).

The major hsps can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch et al., 1985, J. Cell. Biol. 101:1198–1211). In contrast, hsp90 and hsp60 proteins are abundant at normal temperatures in most, but not all, mammalian cells and are further induced by heat (Lai et al., 1984, Mol. Cell. Biol. 4:2802–2810; van Bergen en Henegouwen et al., 1987, Genes Dev. 1:525–531).

Studies on the cellular response to heat shock and other physiological stresses revealed that the hsps are involved not only in cellular protection against these adverse conditions, but also in essential biochemical and immunological processes in unstressed cells. The hsps accomplish different kinds of chaperoning functions. For example, hsp70, located in the cell cytoplasm, nucleus, mitochondria, or endoplasmic reticulum, (Lindquist, S. et al., 1988, Ann. Rev. Genetics 22:631–677) are involved in the presentation of antigens to the cells of the immune system, and are also involved in the transfer, folding and assembly of proteins in normal cells. Hsps are capable of binding proteins or peptides, and releasing the bound proteins or peptides in the presence of adenosine triphosphate (ATP) or low pH.

Other stress proteins involved in folding and assembly of proteins include, for example, protein disulfide isomerase (PDI), which catalyses disulfide bond formation, isomerization, or reduction in the endoplasmic reticulum (Gething et al., 1992, Nature 355:33–45).

Heat shock proteins are among the most highly conserved proteins in existence. For example, DnaK, the hsp70 from $E.$ $coli$ has about 50% amino acid sequence identity with hsp70 proteins from excoriates (Bardwell et al., 1984, Proc. Natl. Acad. Sci. 81:848–852). The hsp60 and hsp90 families also show similarly high levels of intra families conservation (Hickey et al., 1989, Mol. Cell. Biol. 9:2615–2626; Jindal, 1989, Mol. Cell. Biol. 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress.

2.4. Immunogenicities of Heat Shock/Stress Proteins hsp70, hsp90 and gp96

Srivastava et al. demonstrated immune response to methylcholanthrene-induced sarcomas of inbred mice (1988, Immunol. Today 9:78–83). In these studies, it was found that the molecules responsible for the individually distinct immunogenicity of these tumors were identified as cell-surface glycoproteins of 96 kDa (gp96) and intracellular proteins of 84 to 86 kDa (Srivastava, P. K. et al., 1986, Proc. Natl. Acad. Sci. USA 83:3407–3411; Ullrich, S. J. et al., 1986, Proc. Natl. Acad. Sci. USA 83:3121–3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava, P. K. et al., 1988, Immunogenetics 28:205–207; Srivastava, P. K. et al., 1991, Curr. Top. Microbiol. Immunol. 167:109–123). Further, hsp70 was shown to elicit immunity to the tumor from which it was isolated but not to antigenically distinct tumors. However, hsp70 depleted of peptides was found to lose its immunogenic activity (Udono, M., and Srivastava, P. K., 1993, J. Exp. Med. 178:1391–1396). These observations suggested that the heat shock proteins are not immunogenic per se, but form non-covalent complexes with antigenic peptides, and the complexes can elicit specific immunity to the antigenic peptides (Srivastava, P. K., 1993, Adv. Cancer Res. 62:153–177; Udono, H. et al., 1994, J. Immunol., 152:5398–5403; Suto, R. et al., 1995, Science, 269:1585–1588).

The use of noncovalent complexes of stress protein and peptide, purified from cancer cells, for the treatment and prevention of cancer has been described in PCT publications WO 96/10411, dated Apr. 11, 1996, and WO 97/10001, dated Mar. 20, 1997 (see also copending U.S. patent applications Ser. No. 08/796,319 filed Feb. 7, 1997 by Srivastava and Chandawarkar and Ser. No. 08/796,316 filed Feb. 7, 1997 by Srivastava, each of which is incorporated by reference herein in its entirety). Stress protein-peptide complexes can also be isolated from pathogen-infected cells and used for the treatment and prevention of infection caused by the pathogen, such as viruses, and other intracellular pathogens, including bacteria, protozoa, fungi and parasites. See PCT publication WO 95/24923, dated Sep. 21, 1995. Immunogenic stress protein-peptide complexes can also be prepared by in vitro complexing of stress protein and antigenic peptides, and the uses of such complexes for the treatment and prevention of cancer and infectious diseases has been described in PCT publication WO 97/10000, dated Mar. 20, 1997. The use of stress protein-peptide complexes for sensitizing antigen presenting cells in vitro for use in adoptive immunotherapy is described in PCT publication WO 97/10002, dated Mar. 20, 1937.

The purification of stress protein-peptide complexes has been described previously; see for example, PCT Publication WO 95/24923, dated Sep. 21, 1995. For the purpose of preparing a vaccine against cancer, the amount of immunogenic material obtainable for use is directly related to the amount of starting cancer cells. Since only a small number of cancer cells can be obtained from a subject, especially if the cancer is at an early stage, the supply of cancer cells for producing the hsp-peptide complex is often very limited. Although some type of cancer cells can be cultured in vitro, such is less preferable than using complexes known to be representative of the cancer cells in vivo. For commercial production of a vaccine or therapeutic agent, a constant supply of large amounts of hsp-peptide complexes is advantageous. Thus, there is a need for a dependable long-term source of hsp-peptide complexes that does not depend on availability of fresh cell samples from cancer patients. The methods of the present invention do not depend on a large or continuous supply of such cancer cells from a subject, and can be used to provide hsp-peptide complexes even when only a very small amounts of tumor tissue is available from a patient for use.

3. SUMMARY OF THE INVENTION

The present invention relates to methods for producing increased amounts of immunogenic material which can be used for prevention and treatment of cancer. The immunogenic compositions prepared by the methods of the invention comprise noncovalently associated molecular complexes of a heat shock protein (hsp) and an antigenic (or immunogenic) peptide. The complexes prepared by the methods of the invention are intracellularly produced complexes comprising hsps from a selected recombinant host cell and antigenic peptides expressed from cDNAs of a cancer cell; the antigenic peptides of the complex are thus representative of antigenic peptides found in such cancer cell. The present invention provides methods for making a cDNA library from cancer cells, using the cDNA library to produce by recombinant DNA methods in host cells immunogenic hsp-peptide complexes that confer immunity to the cancer cells in an individual to which the complexes are administered.

Generally, the methods of the invention comprise obtaining (e.g., isolating) cancer cells from one or more individuals, preparing RNA from the cancer cells, making cDNA from the RNA, introducing the cDNA into host cells, culturing the host cells so that the cancer-derived cDNAs are expressed, and purifying heat shock protein-peptide complexes from the host cells.

The cDNA prepared from cancer cell RNA, herein referred to as "cancer cDNA", is optionally amplified prior to introduction into a host cell for expression. The cDNAs are optionally inserted into a cloning vector for replication purposes prior to expression. The cDNAs are inserted into an expression vector or intrachromosomally integrated, operatively linked to regulatory element(s) such as a promoter, for purposes of expressing the encoded proteins in suitable host cells in vitro. The cDNAs are introduced into host cells where they are expressed by the host cells, thereby producing intracellularly noncovalent complexes of hsps and peptides (including those peptides encoded by the cancer cDNAs). The recombinant host cells can be cultured on a large scale for production of large amounts of the immunogenic complexes. The cancer cDNA library can be stored for future use (e.g., by lyophilization or freezing), or expanded by replication in a cloning vector in suitable host cells to meet increased demand for the immunogenic complexes.

The immunogenic compositions prepared from the host cells expressing the cancer cDNAs comprise complexes of hsps of the host cell noncovalently associated with peptides, inter alia, those derived from the cancer cells from which the RNA was originally derived. Such complexes can induce an immune response in a patient against the cancer cells that is therapeutically or prophylactically efficacious. Preferably, the patient is the subject from whom the cancer cells used to make cDNA were obtained. Alternatively, the cancer cells can be from one or more subjects different from the patient but having cancer of the same tissue type (e.g., stomach cancer, breast cancer, colon cancer, lung cancer, etc.)

Optionally, host cells for expression of the cancer cDNAs can also be genetically engineered to coexpress recombinantly one or more hsp genes so that increased amounts of complexes comprising immunogenic peptides noncovalently associated with the hsps can be produced. Particular compositions of the invention and their methods of preparation are described in the sections and subsections which follow.

4. BRIEF DESCRIPTION OF THE DRAWINGS

FIG. 1. Flow chart illustrating an exemplary method of the invention of producing hsp-peptide complexes. Optional steps are indicated by a dashed line.

5. DETAILED DESCRIPTION OF THE INVENTION

The present invention contemplates the application of recombinant DNA technology to the preparation of an immunogenic composition that can be used for the prevention and treatment of cancer. The immunogenic compositions prepared by the methods of the invention comprise noncovalently associated molecular complexes containing a heat shock protein (hsp) and an antigenic peptide that is present or that is a portion of a protein that is present in a cancer cell. Such hsp-peptide complexes are capable of inducing a specific immune response in a mammal against the cancer cell.

Immunogenic hsp-peptide complexes are produced naturally in cancer cells. As it is not always possible or feasible to obtain large number of cancer cells, the quantity of the hsp-peptide complexes obtainable from the cancer cells is sometimes very limited. It is therefore an object of the present invention to overcome the potential problem of having a restricted supply of starting cellular material by providing methods for making a cDNA library from cancer cells that is useful for producing large quantities of hsp-peptide complexes in recombinant host cells.

In one embodiment, the invention provides methods for making a cDNA library from RNA of cancer or preneoplastic cells (hereinafter, "cancer cDNA library") and, for using the cancer cDNA library to produce an immunogenic composition comprising noncovalent complexes of antigenic peptides of the cancer or preneoplastic cells and heat shock proteins of the host cells. The present invention will be described in terms of "cancer cells" for case of description, although as will be apparent, the methods of the invention can also be applied using preneoplastic cells, with use for the prevention or inhibition of cancer. The hsp-peptide complexes are recovered and preferably purified from cultures of the recombinant host cells. An exemplary method of the invention of producing hsp-peptide complexes is illustrated in FIG. 1.

In one specific embodiment, the invention provides a method for producing hsp-peptide complexes comprising introducing into one or more host cells cDNA molecules made from RNA molecules of cancer cells, wherein each cDNA molecule is or becomes operably associated with at least one regulatory region that controls expression of the cDNA molecules; culturing the host cells containing the cDNA molecules under conditions such that proteins (including peptides) encoded by the cDNA molecules are expressed by the host cells; and recovering from the host cells complexes of heat shock protein noncovalently associated with one or more peptides.

In another specific embodiment, the invention provides a method for producing hsp-peptide complexes comprising culturing host cells which contain an expression construct comprising a cDNA encoding a cancer protein (e.g., peptide), such that the cancer protein is expressed in the host cells and becomes noncovalently associated with hsps of the host cells, and recovering the hsp-peptide complexes.

The hsp-peptide complexes recovered from recombinant host cells can be purified to achieve a high degree of purity of the complexes. In a specific embodiment, the complexes can be purified to apparent homogeneity by the methods described in section 5.2.

As used herein, preneoplastic cells may include antigenic cells that are infected with a cancer-causing infectious agent, such as a virus but which are not yet neoplastic; or antigenic cells that have been exposed to a mutagen or cancer-causing agent, such as, for example DNA-damaging agents, radiation, etc. Other cells that can be used to make the cDNA library are preneoplastic cells which are in transition from a normal to a neoplastic form as characterized by morphology, physiological or biochemical functions. Preferably, the cancer cells and preneoplastic cells used in the methods of the invention are of mammalian origin. Mammals contemplated by this aspect of the invention include humans, companion animals (e.g., dogs and cats), livestock animals (e.g., sheep, cattle, goats, pigs and horses), laboratory animals (e.g., mice, rats and rabbits), and captive or free wild animals.

In a normal mammalian cell, it has been estimated that there are approximately 30,000 to 120,000 different messenger RNA (mRNA) species present in the cytoplasm (Bishop et al., 1974, Nature 250:199–204; Ryffel et al., 1975, Biochem 14:1379–1385). In various embodiments, the cancer cDNA libraries of the present invention contain at least 30,000, at least 60,000, or at least 90,000 independent cDNAs. Preferably, in order to ensure adequate representation in a cDNA library of all the different RNA species, the cancer cDNA libraries, such as when made from total mRNA, contain at least one order of magnitude more cDNAs than the estimated number of mRNA species, e.g., a cancer cDNA library may contain 300,000 to 1,200,000 independent cDNA clones.

The cancer cDNA library of the invention comprises a pool of cDNAs made from RNA of cancer cells, preferably total polyA+ RNA (mRNA). Preferably, each isolated cancer cDNA is operably associated with at least one regulatory region (e.g., promoter) that controls expression of the cDNA in an appropriate host cell or host organism. Alternatively, the cDNA may be flanked by regions promoting homologous recombination within the host cell so as to insert the cDNA in an intrachromosomal position so that the cDNA is operably associated with at least one regulatory region that controls expression of the cDNA in the host cell or organism.

A library of expression or replicable constructs comprising cancer cDNAs can be amplified in vitro (if desired), aliquoted, and lyophilized or frozen as nucleic acid molecules for future use. To meet increased demand for the hsp-peptide complexes, the library can be thawed and directly introduced into host cells for production of hsp-peptide complexes. Alternatively, the library can be cloned and/or expanded by replication in a cloning vector in an intermediate cells, prior to introduction into suitable host cells for production of hsp-peptide complexes. In effect, the cancer cDNA library captures and preserves the antigenic genetic material that is actively expressed in the cancer cells.

Expression constructs or expression vectors comprising cancer cDNAs can be introduced and maintained in the host cells by any methods known in the art. The cancer cDNAs of the cancer cells are transcribed, translated, and processed if appropriate, in the host cells or host organisms to produce the proteins or peptides of the cancer cells, some of which are antigenic and can induce an immune response when complexed with a stress protein. The term "cancer cDNA host cells" will be used herein to refer to host cells containing cancer cDNA.

Upon expression of the cancer cDNA in a recombinant host cell, one or more proteins (e.g. peptides) of the cancer cells and fragments thereof are produced which become associated with the stress proteins of the host cell to form noncovalent complexes. Because some of the proteins of the cancer cells are antigenic/immunogenic, peptides/proteins that complex with hsps confer specific immunity to a host against the cancer cell in which they are present (see PCT Publication WO 96/10411, dated Apr. 11, 1996). The immunogenicity of such compositions can be tested by methods known in the art and described in Section 5.3. Noncovalent complexes of such cancer peptides with hsps can be used as a vaccine to treat or prevent the type of target cancer from which the antigenic cancer peptide originated. Thus, an immunogenic composition that is useful as a vaccine can be recovered or purified from a culture of recombinant host cells that are expressing cancer cDNAs and producing noncovalent complexes of cancer peptides and hsps.

Depending on needs, the recombinant host cells containing the cancer cDNA library can be pooled and/or aliquoted; or expanded to increase the number of clones containing the library; or archived by freezing down and storing under liquid nitrogen, so that batches of the recombinant host cells can be retrieved and used many times in the future. By culturing the cancer cDNA library cells continuously or in batch, in a suitably large scale, the antigenic peptides that are expressed in the cancer cells can be produced in large amounts in the recombinant host cells. The desirable immunogenic compositions useful for the treatment and prevention of cancer, comprising noncovalent complexes of hsps of the host cells and antigenic proteins/peptides of the cancer cells, can be prepared or purified from a large-scale continuous or batch culture of cancer cDNA host cells. Thus, a cancer cDNA library can provide a consistent, reproducible and abundant source of the useful immunogenic composition.

In various embodiments, any cancer cells, preferably human cancer cells, can be used in the present methods for making a cancer cDNA library. The cancer cells provide the RNAs which encode the proteins that are expressed in the cancer, cells. Cancers which can be treated or prevented with immunogenic compositions prepared by methods of the invention include, but are not limited to, tumors such as sarcomas and carcinomas. Examples of cancers that are amenable to the methods of the invention are listed in Section 5.4.

In one embodiment of the invention, any tissues or cells isolated from a preneoplastic lesion, a cancer, including cancer that has metastasized to multiple remote sites, can be used in the present method. For example, cells found in abnormally growing tissue, circulating leukemic cells, metastatic lesions as well as solid tumor tissue can be used.

In another embodiment, cell lines derived from a preneoplastic: lesion, cancer tissues or cancer cells can also be used, provided that the cells of the cell line have at least one or more antigenic determinants in common with antigens on the target cancer cells. Cancer tissues, cancer cells, cells infected with a cancer-causing agent, other preneoplastic cells, and cell lines of human origin are preferred. Preferably, cancer cells are used that are excised from the patient to which ultimately the complexes are to be administered, although this need not be the case (e.g., the cancer cells can be from one or more different individuals).

Cancer and preneoplastic cells can be identified by any method known in the art. For example, cancer cells can be identified by morphology, enzyme assays, proliferation assays, cytogenetic characterization, DNA mapping, DNA sequencing, the presence of cancer-causing virus, or a history of exposure to mutagen or cancer-causing agent, imaging, etc. Cancer and preneoplastic cells can be isolated by any method known in the art. For example, cancer cells can be obtained by surgery, endoscopy, or other biopsy techniques. If some distinctive characteristics of the cancer cells are known, they can also be obtained or purified by any biochemical or immunological methods known in the art, such as but not limited to affinity chromatography, and fluorescence activated cell sorting (e.g., with fluorescently tagged antibody against an antigen expressed by the cancer cells).

There is no requirement that a clonal or homogeneous or purified population of cancer cells be used to make a cancer cDNA library. Cancer tissues, cancer cells or cell lines may be obtained from a single individual or pooled from several individuals. It is not essential to use cells of the ultimate target in vivo (e.g., cells from the tumor of the intended recipient), so long as at least one or more antigenic determinants on the target cancer cells is present on the cells used in making the cancer cDNA library. In addition, cells derived from distant metastases may be used to prepare an immunogenic composition against the primary cancer. A mixture of cells can be used provided that a substantial number of cells in the mixture are cancer cells and share at least one antigenic determinant with the target cancer cell. In a specific embodiment, the cancer cells to be used in constructing the cDNA library are purified.

Noncovalent hsp-peptide complexes derived directly from a cancer can be used to elicit in a subject a specific immune response against the same cancer, and thus, are useful for the prevention and treatment of the cancer. See, for example, PCT Publications WO 96/10411 and WO97/10001. The present invention provides methods for preparing immunogenic compositions comprising noncovalent complexes of hsps and antigenic proteins or peptides of a cancer. Accordingly, such noncovalent complexes are useful for the prevention and treatment of the target cancer in a subject. The immunogenic compositions prepared by the claimed method can enhance the immunocompetence of an individual and elicit specific immunity against both preneoplastic and neoplastic cells. Such immunogenic compositions are also capable of preventing the development of tumors and inhibiting the growth and progression of tumor cells. The immunogenic compositions can be used to induce an inflammatory reaction at the tumor site and ultimately cause a regression of the tumor burden in the cancer patients treated. The immunogenic compositions can also be administered autologously to the individual from whom the cancer tissues were obtained, or to individuals at enhanced risk of cancer due to familial history or environmental risk factors.

The antigenic peptides of the present invention are associated with hsps inside a cancer cell or a recombinant host cell expressing a cancer cDNA. Such antigenic peptide can be a fragment of an antigenic protein expressed in the cancer cell, such as for example, fragment of a tumor-specific antigen or tumor associated antigen. Such antigenic peptides are produced in cancer cDNA host cells that are expressing the cloned cancer cDNAs. However, it is not necessary to isolate or characterize or even know the identities of these antigens in advance of using the present methods. In addition, the cancer cDNAs that are expressed recombinantly in the host cells need not comprise full-length coding sequences although such is preferable.

Heat shock proteins, which are referred to interchangeably herein as stress proteins, useful in the treatment and prevention of cancer, can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH; or it is a protein showing at least 35% homology with any cellular protein having any of the above properties. The hsps in the complexes that can be prepared by the present invention include but are not limited to, hsp70, hsp90, gp96, protein disulfide isomerase alone or in combination. Preferably, the hsps are human hsps. Preferred complexes comprise human hsp60, hsp70, or hsp90, protein disulfide isomerase, noncovalently bound to a human protein antigen. In a specific embodiment, the complex comprises an hsp called gp96 which is present in the endoplasmic reticulum of eukaryotic cells and is related to the cytoplasmic hsp90s.

Three major families of hsp, namely hsp60, hsp70 and hsp90, have been identified so far. In addition, protein disulfide isomerase (PDI), and other proteins in the endoplasmic reticulum that contain thioredoxin-like domain(s), such as but not limited to ERp72 and ERp61, are also encompassed. It is contemplated that hsp-peptide complexes comprising members of all of these families, including but not limited to PDI-peptide complexes, can be prepared by the practice of the instant invention.

It has been discovered that the hsp60, hsp70, hsp90 and protein disulfide isomerase families are composed of proteins that are related to the stress proteins in sequence, for example, having greater than 35% amino acid identity, but whose expression levels are not altered by stress. Therefore it is contemplated that the definition of stress or heat shock protein, as used herein, embraces other proteins, muteins, analogs, and variants thereof having at least 35% to 55%, preferably 55% to 75%, and most preferably 75% to 85% amino acid identity with members of these families whose expression levels in a cell are enhanced in response to a stressful stimulus.

In one embodiment of the invention, the hsps in the hsp-peptide complexes prepared from cancer cDNA host cells are native to the host cells, i.e, the hsps that are noncovalently associated with recombinant antigenic peptides of the cancer cells are naturally occurring in the host cells.

In another embodiment, the hsp in the hsp-peptide complex is a recombinant hsp produced by cancer cDNA host cells that are genetically engineered to express the recombinant hsp. Such recombinant hsps are noncovalently associated with recombinant antigenic peptides in host cells to form hsp-peptide complexes. Such recombinant hsps may also be fused to a heterologous polypeptide, such as an immunoglobulin constant region, which can facilitate purification of the noncovalent complex. The genetically engineered host cells may contain one or more copies of a nucleic acid sequence comprising a sequence that encodes a hsp, operably associated with regulatory region(s) that drive expression of the hsp nucleic acid sequence in the host cell. Any nucleic acid sequence encoding a hsp, including cDNA and genomic DNA, can be used. It is preferred that the recombinant hsp produced in the host cell or library cell is of the same species as the intended recipient of the immunogenic composition. Recombinant human hsp is most preferred.

5.1. Preparation of Cancer cDNA Library

Described herein are methods for the construction of a cancer cDNA library. Specifically described are the making of complementary DNA (cDNA) from cancer cell RNA, the insertion of cDNAs into an appropriate cloning vector, and the introduction of the cloned cDNAs into an appropriate host organism for propagation of the cancer cDNA library and/or for the production of hsp-peptide complexes.

The procedures described in standard treatises, e.g., Methods in Enzymology, 1987, volume 154, Academic Press; Sambrook et al., 1989, Molecular Cloning—A Laboratory Manual, 2nd Edition, Cold Spring Harbor Press, New York; and Ausubel et al., Current Protocols in Molecular Biology, Greene Publishing Associates and Wiley Interscience, New York, may be followed to carry out routine molecular biology reactions used in constructing and producing the cancer cDNA libraries. Methods described in detail infra are for illustration only and not by way of limitation. Various cDNA preparation and cDNA cloning systems that are commercially available may also be used according to the manufacturer's instructions for making a cancer cDNA library of the invention.

5.1.1. Preparation of RNA

Total ribonucleic acid (RNA) may be isolated from cancer cells by a variety of methods known in the art depending on the source and amount of cancer or preneoplastic cells. It is preferable to obtain good quality RNA that is of high molecular weight in order to construct cDNA libraries that are fully representative of the expressed genetic information of the cancer cells. To prepare high quality RNA, methods that provide complete lysis of cancer cells, and rapid inactivation of nucleases are preferred.

One principal method, though certainly not the only one that can be used in the present invention, uses the strong chaotropic agent, guanidinium isothiocyanate, with a mild detergent and 2-mercaptoethanol or dithiothreitol to denature proteins and inactivate nucleases, followed by purification of the RNA by ultracentrifugation (Chirgwin et al., 1979, Biochem 24:5294; Sadler et al., 1992, Curr Genet 21:409–416). A single-step method (Chomczynski & Sacchi, 1987, Anal Biochem 162:156–159; Chomczynski, 1989, U.S. Pat. No. 4,843,155) may also be used especially when isolating RNA from small quantities of cellular material.

Preferably, total RNA isolated from cancer cells is further purified before conversion into complementary DNA (cDNA). Since the vast majority of eukaryotic messenger RNA (mRNA) molecules contain tracts of poly(adenylic) acid (polyA) at the 3' end, it can be enriched by affinity chromatography using oligo-dT cellulose (Aviv & Leder, 1972, Proc. Natl. Acad. Sci., 69:1408–1412). Total RNA is denatured to expose the poly-A tails. Poly-A+ RNA is then bound to oligo-dT cellulose, with the remainder of the RNA washing through. The poly-A+ RNA is eluted by removing salt from the solution. This step may be repeated to further enrich for messenger RNA. A wide variety of oligo-dT matrices in different configurations may also be used, including but not limited to, simple gravity columns, paramagnetic particles, and spin columns. Substituted oligo-dT, such as biotinylated oligo-dT, may also be used. The quantity and quality of RNA thus obtained may be determined by methods such as formaldehyde agarose gel electrophoresis. The use of RNA enriched for poly-A+ RNA is most preferred.

5.1.2. Preparation of Cancer cDNAs

Conversion of RNA into double-stranded cDNA can be accomplished by a number of different procedures well known in the art. See for example, Okayama & Berg, 1982, Mol. Cell Biol. 2:161–1.70; Gubler & Hoffman, 1983, Gene 25:263–269; and Huse & Hansen, 1988, Strategies (stratagene) 1:1–3.

The first step in the making of cDNA involves the oligonucleotide-primed synthesis of a first strand cDNA by a reverse transcriptase. For example, mRNA hybridized to an oligo-dT primer can be copied into DNA by a reverse transcriptase, such as AMV reverse transcriptase, MMLV reverse transcriptase, or Superscript (Kotewicz et al., 1988, Nucleic Acid Res. 16:265–277). Random hexamers may be used to prime first-strand synthesis from internal sites within the mRNA instead of oligo-dT primers resulting in shorter cDNAs which are enriched for the 5' ends of long messenger RNAs.

The next step in the process involves synthesizing the second strand cDNA and producing suitable DNA ends for insertion in a cloning vector. Briefly, for (example, the second strand cDNA may be synthesized using E. coli DNA polymerase I, Klenow fragment using the RNA-DNA as a template. The RNA in the RNA-DNA hybrid can be removed with RNase H, and gaps in the newly synthesized second strand cDNA can be filled in by E. coli DNA polymerase I. The fragments of second strand cDNAs thus produced are ligated with E. coli DNA ligase to form a contiguous second strand cDNA.

After second strand DNA synthesis, the double stranded cDNA requires further repair with enzymes, such as RNase H, RNase A, T4 DNA polymerase and E. coli DNA ligase, to form perfectly matched strands (i.e., having "flush" or "blunt" ends).

In cases where the amount of starting cellular material is very limited, all the cDNAs made from the cancer cell can be amplified in vitro, prior to cloning, by nucleic acid amplification methods known in the art, such as polymerase chain reaction (PCR) and ligation chain reaction (LCR). Generally, first strand oligo-dT primed cDNA obtained by a standard method is extended with a oligo-dG tail by terminal transferase, and a second primer containing a oligo-dC segment is used to prime second strand synthesis with a thermostable DNA polymerase. This procedure produces a double-stranded cDNA population each molecule of which is bracketed by two oligonucleotides of known sequence. Using the appropriate set of primers, standard PCR can be used to amplify all the cDNAs made from the cancer cell. See, for example, U.S. Pat. Nos. 4,683,202, 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220; Tam et al., 1989, Nucleic Acid Res. 17:1269; Belyavsky et al., 1989, Nucleic Acid Res. 17:2919–2932. In specific embodiments of the invention, RT-PCR can be used to generate amplified cDNAs from the RNAs of the cancer cell (See, e.g., Domec et al., 1990, Anal Biochem, 188:422–426; Van Gelder et al., 1990, Proc. Natl. Acad. Sci., 87:1663–1667).

In order to attach DNA sequences with regulatory functions, such as promoters, to the double-stranded cDNAs, or to insert the double stranded cDNAs into the cloning site of a vector, linkers or adaptors providing the appropriate compatible restriction sites may be ligated to the ends of the cDNAs by techniques well known in the art (Wu et al., 1987, Methods in Enzymol 152:343–349). Cleavage with a restriction enzyme can be followed by modification to create blunt ends by digesting back or filling in single-stranded DNA termini before ligation. Alternatively, a desired restriction enzyme site can be introduced into a cDNA by amplification of the cDNA by use of PCR with primers containing the desired restriction enzyme site. Homopolymeric tailing may also be used to generate the appropriate ends in the cDNAs for cloning (Eschenfeldt et al., 1987, Methods in Enzymol, 152:337–342).

Linkers are synthetic duplex molecules that are blunt at both ends. Prior to ligation of a linker to double-stranded cDNAs, in order to protect internal restriction sites of the cDNAs from cleavage by the restriction enzyme digestion (required to allow ligation of the vector and linker), the cDNAs are methylated with the appropriate DNA modification system associated with the given restriction enzyme. For example, double-stranded cDNA can be methylated by *E. coli* methylase, ligated to *E. coli* linkers, and digested with EcoRI to generate EcoRI sites at the ends of the cDNAs. The linkered cDNA can be inserted into a cloning vector with a EcoRI site directly.

Adaptors are short partially duplex DNA molecules having a phosphorylated blunt end for ligation to the ends of the cDNAs, a double-stranded regions optionally containing one or more rare restriction sites, and a single stranded segment that forms a compatible ends ready for insertion into a cloning vector with a corresponding restriction site. In cases where an adaptor is used to modify the ends of the cDNAs, the methylation and restriction digestion steps described above can be bypassed.

Another well known strategy for generation of cDNAs that have unique ends for use in orientation-specific or directional cloning may also be used. This method uses a cloning vector with an appropriately positioned promoter to increase the likelihood of expressing the cloned cDNAs in the correct orientation by a factor of two.

Briefly, for example, directional cloning can be carried out by hybridizing mRNA to a linker-primer that has a poly-dT tract and internal methylation-sensitive restriction sites, such as XhoI. The linker-primer is extended using a reverse transcriptase and a nucleotide mix in which dCTP is replaced with methylated-dCTP. When second strand synthesis is completed, adaptors containing a desired restriction site, such as EcoRl, can be ligated to the double-stranded cDNAs, which is then treated with XhoI. A XhoI site at the 3' end of the cDNAs is generated while the internal methylated XhoI sites remain uncut. Such cDNAs having a desired site, such as EcoRI, at the 5' end and an XhoI site at the 3' end can be cloned unidirectionally into a vector such that the 5' end of the cDNAs are consistently positioned downstream from a promoter.

Alternatively, an adapter-primer can be used which contains a poly-dT tract adjacent to a rare restriction site, such as NotI. Subsequent procedure is carried out as for oligo-dT primed synthesis using unsubstituted nucleotides as described above, except that the final cDNAs with adaptors attached (such as EcoRI adaptors) is digested with the rare restriction enzyme, resulting in cDNAs with a desired restriction site, such as EcoRI, at one end, and the rare restriction site at the other end. Such cDNAs having an EcoRI site at the 5' end and a rare restriction site, such as NotI, at the 3' end can be cloned unidirectionally into a vector containing a EcoRI/NotI cloning site wherein a promoter can be positioned upstream of the EcoRI cloning site.

Linkered or adapted cDNAs can be passed over a size exclusion column such as SEPHAROSE™ CL-4B to remove unligated linkers or adaptors and other low molecular weight material that would interfere with the ensuing manipulations. Optionally, fractionation of the linkered or adapted cDNAs, for example, by agarose gel electrophoresis, can be carried out to enrich for cDNA of a particular size range.

The double stranded cDNAs made from RNAs of the cancer cells, also referred to herein as cancer cDNAs, can be ligated to DNA sequences with regulatory functions, and/or inserted into a cloning vector for propagation prior to expression in suitable host cells, or directly inserted into an expression vector or flanked by sequences promoting intrachromosomal insertion, for expression in suitable host cells.

An expression construct, as used herein, refers to a polynucleotide comprising cancer cDNA sequences operably associated with one or more regulatory regions which enables expression of the cancer cDNA in an appropriate host cell. "Operably-associated" refers to an association in which the regulatory regions and the cDNA sequence to be expressed are joined and positioned in such a way as to permit transcription, and ultimately, translation.

The regulatory regions necessary for transcription of the cancer cDNAs can be provided by an expression construct. A translation initiation codon (ATG) may also be provided if the cancer cDNA fragments without their cognate initiation codon are to be expressed. In a compatible host-construct system, cellular transcriptional factors, such as RNA polymerase, will bind to the regulatory regions on the expression construct to effect transcription of the cancer cDNA in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-noncoding sequences involved with initiation of -transcription and translation, such as the TATA box, capping sequence, CAAT sequence, and the like. The noncoding region 3' to the coding sequence may contain transcriptional termination regulatory sequences, such as terminators and polyadenylation sites. In order to be "operably-associated", it is not necessary that the regulatory region and the cancer cDNA sequences be immediately adjacent to one another. Regulatory regions suitable for gene expression are well known in the art (see Section 5.1.3).

Both constitutive and inducible regulatory regions may be used for expression of the cancer cDNA. It may be desirable to use inducible promoters when the conditions optimal for growth of the host cells and the conditions for high level expression of the cancer cDNA are different. This use of an inducible regulatory region may be particularly desirable if some of the proteins encoded by the cancer cDNAs confer growth advantages or disadvantage to the recombinant host cells expressing them. Examples of useful regulatory regions are provided in the next section below.

The expression constructs comprising the cancer cDNAs operably associated with regulatory regions can be directly introduced into appropriate host cells for expression and production of hsp-peptide complexes without further cloning. See, for example, U.S. Pat. No. 5,580,859. The expression constructs can also contain DNA sequences that facilitate integration of the cancer cDNAs into the genome of the host cell, e.g., via homologous recombination. In this instance, it is not necessary to employ an expression vector comprising a replication origin suitable for appropriate host cells in order to propagate and express the cancer cDNAs in the host cells.

The expression constructs can also comprise at both ends specific oligonucleotide sequences, which may be utilized as primers to amplify the cancer cDNAs by polymerase chain reaction (PCR). The design of the primer sequences for DNA amplification and the ligation of the primer sequences to the cancer cDNAs can be carried out by any methods known in the art, including those described above employing linkers and adaptors. The amplification can be carried out, e.g., by use of a Perkin-Elmer Cetus thermal cycler and Taq polymerase (Gene Amp™). Such a library of expression constructs cDNAs can be amplified and maintained in vitro, without the use of DNA sequences that propagate the polynucleotide within living cells. A library of expression constructs comprising cancer cDNAs can be archived or stockpiled by DNA amplification, and the resulting nucleic acid molecules lyophilized and/or frozen in aliquots for storage. Depending on needs, an aliquot of the library of expression constructs can be thawed and introduced directly into host cells for expression. Such expression constructs can be used for expression of cancer cDNAs transiently in recombinant host cells. This approach may be particularly useful if the recombinant host cells may not be amenable to long term culture or prolonged production of hsp-peptide complexes.

In various embodiments of the invention, cancer cDNAs or expression constructs comprising cancer cDNAs can be inserted into) an expression vector for propagation and expression in host cells as described below.

5.1.3. Host-Vector Expression System

Described herein are systems of vectors and host cells that can be used for cloning and expression of cancer cDNAs. An expression vector is a cloning vector that can be used for maintenance and expression of cancer cDNAs in an appropriate host cell. Any cloning vector known in the art can be used to propagate the cancer cDNAs. A variety of cloning vectors may be used in the present invention which include, but are not limited to, plasmids, cosmids, phage, phagemids, or modified viruses. Typically, such cloning vectors comprise a functional origin of replication for propagation of the vector in an appropriate host cell, one or more restriction endonuclease sites for insertion of the cancer cDNAs, and one or more selection markers. The cloning vector must be used with a compatible host cell which may be derived from a prokaryotic or an eukaryotic organism including but not limited to bacteria, yeasts, insects, mammals, and humans.

Expression constructs and vectors are introduced into host cells for the purpose of expressing the cancer cDNAs. Any cell type that produces stress proteins and is compatible with the expression vector may be used, including those that have been cultured in vitro or genetically engineered. Host cells broadly encompass cells of unicellular organisms, such as bacteria, fungi, and yeast, and of multicellular organisms, such as insects and animals including but not limited to birds, mammals and humans. Host cells may be obtained from normal or affected subjects, including healthy humans and patients, private laboratory deposits, public culture collections such as the American Type Culture Collection, or from commercial suppliers.

Different host cells have characteristic and specific mechanisms for the post-translational processing and modification of proteins. A host cell may be chosen which modifies and processes the expressed gene products in a specific fashion similar to the cancer cell. Such modifications (e.g., glycosylation) and processing (e.g., cleavage) of cancer cDNA-encoded proteins may enhance the antigenicity of the proteins. In a specific embodiment, normal cells from the same type of tissue from which the cancer developed may be used. It is preferable that the type of host cell used in the present invention has been used for expression of heterologous genes, and is reasonably well characterized and developed for large-scale production processes. It is also preferable that the type of host cell is non-adherent to surfaces of cell culture containers, such as plastic, so as to facilitate easy harvesting of the cells. In a specific embodiment, the host cells are the same species as a patient from which the RNA for making cancer DNA is obtained, and/or as the patient to whom the hsp-peptide complexes are subsequently administered.

Vectors based on $E.\ coli$ are the most popular and versatile systems for high level expression of foreign proteins (Makrides, 1996, Microbiol Rev, 60:512–538). Non-limiting examples of regulatory regions that can be used for expression in $E.\ coli$ may include but not limited to lac, trp, lpp, phoA, recA, tac, T3, T7 and $\lambda P_L$ (Makrides, 1996, Microbiol Rev, 60:512–538). Non-limiting examples of prokaryotic expression vectors may include the $\lambda$gt vector series such as $\lambda$gt11 (Huynh et al., 1984 in "DNA Cloning Techniques", Vol. I: A Practical Approach (D. Glover, ed.), pp. 49–78, IRL Press, Oxford), and the pET vector series (Studier et al., 1990, Methods Enzymol, 1851:60–89). However, a potential drawback of a prokaryotic host-vector system is the inability to perform many of the post-translational processing of mammalian cells. Thus, an eukaryotic host-vector system is preferred, a mammalian host-vector system is more preferred, and a human host-vector system is the most preferred.

For expression of cancer cDNAs in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), $\beta$-interferon gene, and hsp70 gene (Williams et al., 1989, Cancer Res. 49:2735–42; Taylor et al., 1990, Mol. Cell Biol., 10:165–75). It may be advantageous to use heat shock promoters or stress promoters to drive expression of the cancer cDNA in recombinant host cells. In this instance, the proteins of the cancer cells can be coordinately expressed with heat shock proteins or stress proteins of the recombinant host cell by exposure to the appropriate stress, such as high temperature.

The efficiency of expression of the cancer cDNA in a host cell may be enhanced by the inclusion of appropriate transcription enhancer elements in the expression vector, such as those found in SV40 virus, Hepatitis B virus, cytomegalovirus, immunoglobulin genes, metallothionein, $\beta$-actin (see Bittner et al., 1987, Methods in Enzymol. 153:516–544; Gorman, 1990, Curr. Op. in Biotechnol. 1:36–47).

The expression vector may also contain sequences that permit maintenance and replication of the vector in more than one type of host cell, or integration of the vector into the host chromosome. Such sequences may include but are not limited to replication origins, autonomously replicating sequences (ARS), centromere DNA, and telomere DNA. It may also be advantageous to use shuttle vectors; which can be replicated and maintained in at least two types of host cells.

In addition, the expression vector may contain selectable or screenable marker genes for initially isolating, identifying or tracking host cells that contain cancer cDNA. For long term, high yield production of hsp-peptide complexes, stable expression in mammalian cells is preferred. A number of selection systems Ray be used for mammalian cells, including but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

A number of viral-based expression systems may also be utilized with mammalian cells to make the cancer cDNA libraries. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655–3659).

Alternatively, the vaccinia 7.5K promoter may be used. (See, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-PCD (Spickofsky et al., 1990, DNA Prot Eng Tech 2:14–18); pDR2 and λDR2 (available from Clontech Laboratories). The expression vector pDR2 carries the EBV origin which confers stable episomal maintenance to the vector when activated by EBNA-1. Extremely high transfection efficiencies up to $10^{-1}$ can be obtained when pDR2 is transfected into cell Lines which express EBNA-1. Host cells can be rendered proficient for high-efficiency transfections by first transfecting the host cells with an expression construct that produces EBNA-1.

Cancer cDNA libraries may also be made with a retrovirus-based expression cloning system. Retroviruses, such as Moloney murine leukemia virus, can be used since most of the viral gene sequence can be removed and replaced with cancer cDNA while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The cancer cDNA is inserted into a position between the 5' LTR and 3' LTR, such that transcription from the 5' LTR promoter transcribes the cloned cancer cDNA. The 5' LTR comprises a promoter, including but not limited to an LTR promoter, an R region, a U5 region and a primer binding site, in that order. Nucleotide sequences of these LTR elements are well known in the art. A heterologous promoter as well as multiple drug selection markers may also be included in the expression vector to facilitate selection of infected cells. See, McLauchlin et al., 1990, Prog Nucleic Acid Res and Molec Biol 38:91–135; Morgenstern et al., 1990, Nucleic Acid Res 18:3587–3596; Choulika et al., 1996, J Virol 70:1792–1798.

Other useful eukaryotic host-vector system may include yeast and insect systems. In yeast, a number of vectors containing constitutive or inducible promoters may be used with Saccharomyces cerevisiae (baker's yeast), Schizosaccharomyces pombe (fission yeast), Pichia pastoris, and Hansenula polymorpha (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In an insect system, Autographa californica nuclear polyhydrosis virus (AcNPV) a baculovirus, can be used as a vector to express cancer cDNA in Spodoptera frugiperda cells. The cancer cDNA sequences may be cloned into non-essential regions (for example the polyhedrin gene) of the virus and placed under control of an ACNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non--limiting examples of useful vectors are pCDM8, λDR2 (see Appendix 5 of Current Protocols in Molecular Biology, 1988, Ed. Ausubel et al., Greene Publish. Assoc. & Wiley Interscience, which is incorporated herein by reference). Preferred mammalian host cells include but are not limited to those derived from humans, monkeys and rodents, such as chinese hamster ovary (CHO) cells, NIH/3T3, COS, HeLa, Daudi, 293, 293-EBNA, VERO, etc. (see, for example, Kriegler M. in "Gene Transfer and Expression: A Laboratory Manual", New York, Freeman & Co. 1990).

By way of example, an exemplary expression host-vector system is λDR2 which is a lambda bacteriophage-based cloning vector coupled with a mammalian expression plasmid. Advantages of this system include the utilization of highly efficient lambda in vitro packaging systems for initially generating a library in *E. coli* hosts. Size selection may not be required since the packaging system only accepts inserts in a certain size range. Lambda vectors generally provide greater ease in amplification and storage. The initial library in *E. coli* may be amplified to produce supercoiled plasmid DNA which may be used in high efficiency transformation methods for introduction into other expression host organisms. For example, λDR2 uses the lox P mediated site-specific recombination to excise the expression vector pDR2 containing a cDNA insert from lambda clones which can recircularize to generate a plasmid. The plasmid pDR2 contains eukaryotic regulatory regions based on the Epstein-Barr virus and selection markers that allows direct introduction of the cDNA inserts as a library into permissive human host cells at high efficiency.

5.1.4. Production of cDNA Library

Expression constructs containing cloned cancer cDNA can be introduced into the host cell by a variety of techniques known in the art, including but not limited to, for prokaryotic cells, bacterial transformation (Hanahan, 1985, in DNA Cloning, A Practical Approach, 1:109–136), and for eukaryotic cells, calcium phosphate mediated transfection (Wigler et al., 1977, Cell 11:223–232), liposome-mediated transfection (Schaefer-Ridder et al., 1982, Science 215:166–168), electroporation (Wolff et al., 1987, Proc Natl Acad Sci 84:3344), and microinjection (Cappechi, 1980, Cell 22:479–488).

For long term, high yield production of hsp-peptide complexes, stable expression in mammalian cells is preferred. Cell lines that stably express hsp-peptide complexes may be engineered by using a vector that contains a selectable marker. By way of example but not limitation, following the introduction of the expression constructs, engineered cells may be allowed to grow for 1–2 days in an enriched media, and then are switched to a selective media. The selectable marker in the expression construct confers resistance to the selection and optimally allows cells to stably integrate the expression construct into their chromosomes and to grow in culture and to be expanded into cell lines.

The recombinant host cells may be cultured under standard conditions of temperature, incubation time, optical density, and media composition. Alternatively, the recombinant host cells may be cultured under conditions emulating the nutritional and physiological requirements of the cancer cell from which the cancer cDNA was derived. However, conditions for maintenance and production of a cancer cDNA library may be different from those for expression of antigenic proteins or peptides. Modified culture conditions and media may also be used to enhance production of hsp-peptide complexes. For example, the host cells containing cancer cDNA may be exposed to heat or other environmental stress, or chemical stress prior to purification of the hsp-peptide complexes. Any techniques known in the art may be applied to establish the optimal conditions for producing hsp-peptide complexes.

5.2. Purification of Hsp-Peptide Complexes

The protocols described hereinbelow may be used to recover and purify hsp-peptide complexes from any mammalian cells, for example, human cells, containing an expression construct comprising a cancer cDNA.

5.2.1. Preparation and Purification of Hsp90-peptide Complexes

The purification of hsp70-peptide complexes has been described previously, see, for example, Udono et al., 1993, J. Exp. Med. 178:1391–1396. A procedure that may be used, presented by way of example but not limitation, is as follows:

Initially, recombinant host cells are suspended in 3 volumes of 1X Lysis buffer consisting of 5 mM sodium phosphate buffer (pH 7), 150 mM NaCl, 2 mM CaCl$_2$, 2 mM MgCl$_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A SEPHAROSE™ equilibrated with phosphate buffered saline (PBS) containing 2 mM Ca$^{2+}$ and 2 mM Mg$^{2+}$. When the cells are lysed by mechanical shearing the supernatant is diluted with an equal volume of 2X lysis buffer prior to mixing with Con A SEPHAROSE™. The supernatant is then allowed to bind to the Con A SEPHAROSE™ for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC™ ion exchange chromatography column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen).

Fractions strongly immunoreactive with the anti-hsp70 antibody are pooled and the hsp70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a SEPHADEX™ G25 column (Pharmacia). To achieve a higher degree of purity (e.g., greater than 80% by weight), the hsp70 preparation thus obtained can be repurified through the Mono Q FPCL Column as described above. The hsp70-peptide complex can be purified to apparent homogeneity using this method. Typically 1 mg of hsp70-peptide complex can be purified from 1 g of cells or tissue.

An alternative method for purification of hsp70-peptide complexes from cancer cDNA host cells is as follows:

A 10 ml cell pellet of recombinant host cells are homogenized in 40 ml hypotonic buffer (10 mM NaHCO$_3$, 0.5 mM PMSF, pH7.1) by Dounce homogenization. Then, the lysate is centrifuged at 100,000 x g for 90 minutes. The supernatant is collected and the buffer is changed to buffer D (20 mM Tris-acetate, 20 mM NaCl, 15 mM B-mercaptoethanol, 3 mM MgCl$_2$, 0.5 mM PMSF, pH7.5) by passing through a PD-10 column (SEPHADE™ G-25, Pharmacia Biotech., Piscataway, N.J.). The sample is applied directly to an ADP-agarose column (Sigma Chemical Co., St. Louis, Mo.)

(5 ml) equilibrated with buffer D. The column is washed with buffer D containing 0.5M NaCl and then buffer D alone until no more protein could be detected by the Bradford protein assay (BioRad, Richmond, Calif.). Finally the column is incubated with buffer D containing 3 mM ADP (Sigma Chemical Co., St. Louis, Mo.) at room temperature for 30 minutes and subsequently eluted with the same buffer (25 ml). The buffer of the eluate is changed again with a PD-10 column to FPLC™ ion exchange chromatography buffer (20 mM Na phosphate, 20 mM NaCl, pH7.0). Then the proteins in the eluate are resolved on a FPLC™ ion exchange chromatography system (Mono Q, Pharmacia) and eluted by a 20–60 mM NaCl gradient. The yield of hsp70 from a 10 ml cell pellet is 500 μg to 1 mg.

5.2.2. Preparation and Purification of Hsp90-peptide Complexes

A procedure that can be used, presented by way of example and not limitation, is as follows:

Initially, recombinant host cells are suspended in 3 volumes of 1X Lysis buffer consisting of 5 mM sodium phosphate buffer (pH 7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A SEPHAROSE™ equilibrated with PBS containing 2 mM $Ca^{2+}$ and 2 mM $Mg^{2+}$. When the cells are lysed by mechanical shearing the supernatant is diluted with an equal volume of 2X lysis buffer prior to mixing with Con A SEPHAROSE™. The supernatant is then allowed to bind to the Con A SEPHAROSE™ for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC™ ion exchange chromatography column equilibrated with lysis buffer. The proteins are then eluted with a salt gradient of 200 mM to 600 mM NaCl.

The eluted fractions are fractionated by SDS-PAGE and fractions containing the hsp90-peptide complexes are identified by immunoblotting using an anti-hsp90 antibody, such as 3G3 (Affinity Bioreagents). An apparently homogenous reparation of hsp90-peptide complexes can be obtained using this procedure. Typically, 150–200 μg of hsp90-peptide complex can be purified from 1 g of cells or tissue.

5.2.3. Preparation and Purification of gp96-peptide Complexes

A procedure that can be used, presented by way of example and not limitation, is as follows:

A pellet of recombinant host cells is resuspended in 3 volumes of buffer consisting of 30 mM sodium bicarbonate buffer (pH 7.5) and 1 mM PMSF and the cells allowed to swell on ice 20 minutes. The cell pellet is then homogenized in a Dounce homogenizer (the appropriate clearance of the homogenizer will vary according to each cells type) on ice until >95% cells are lysed.

The lysate is centrifuged at 1,000 g for 10 minutes to remove unbroken cells, nuclei and other debris. The supernatant from this centrifugation step then is recentrifuged at 100,000 g for 90 minutes. The gp96-peptide complex can be purified either from the pellet after centrifugation at 100,000 g or from the supernatant.

When purified from the supernatant, the supernatant is diluted with equal volume of 2X lysis buffer and the supernatant mixed for 2–3 hours at 4° C. with Con A SEPHAROSE™ equilibrated with PBS containing 2 mM $Ca^{2+}$ and 2 mM $Mg^{2+}$. Then, the slurry is packed into a column and washed with 1X lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono Q FPLC™ ion exchange chromatography column (Pharmacia) equilibrated with a buffer containing 5 mM sodium phosphate, pH 7. The proteins then are eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-SEPHAROSET™ purification after the Con A purification step but before the Mono Q FPLC™ ion exchange chromatography step.

In the first optional step, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A SEPHAROSE™ and the procedure followed as before.

In the second optional step, the gp96 containing fractions eluted from the Con A column are pooled and the buffer exchanged for 5 mM sodium phosphate buffer, pH 7, 300 mM NaCl by dialysis, or preferably by buffer exchange on a SEPHADEX™ G25 column. After buffer exchange, the solution is mixed with DEAE-SEPHAROSE™ previously equilibrated with 5 mM sodium phosphate buffer, pH 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 nM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the Mono Q FPLC™ ion exchange chromatography column (Pharmacia) equilibrated with 5 mM sodium phosphate buffer, pH 7 and the protein that binds to the Mono Q FPLC™ ion exchange chromatography column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10 to 20 μg of gp96 can be isolated from 1 g cells or tissue.

5.2.4. Preparation and Purification of PDI-peptide Complexes

A procedure that can be used, presented by way of example and not limitation, is as follows:

A pellet of recombinant host cells is resuspended in 3 volumes of buffer consisting of 30 mM sodium bicarbonate buffer (pH 7.5) and 1 mM PMSF and the cells allowed to swell on ice 20 minutes. The cell pellet is then homogenized in a Dounce homogenizer (the appropriate clearance of the homogenizer will vary according to each cells type) on ice until >95% cells are lysed.

The lysate is centrifuged at 1,000 g for 10 minutes to remove unbroken cells, nuclei and other debris. The supernatant from this centrifugation step then is recentrifuged at 100,000 g for 90 minutes. The supernatant is brought to a final concentration of 80% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The resulting pellet is harvested and dissolved in PBS containing 2 mM $Ca^{2+}$ and 2 mM $Mg^{2+}$ (2X lysis buffer). The solution is mixed for 2–3 hours at 4° C. with Con A SEPHAROSE™ equilibrated with PBS containing 2 mM $Ca^{2+}$ and 2 mM $Mg^{2+}$ and the slurry is packed into column and washed with 1X lysis buffer until the $OD_{280}$ drops to baseline. The flow-through is collected and passed through a PD-10 column (Pharmacia) to change the buffer to 0.025M sodium citrate (pH 5.1). The solution is loaded onto a CM-Sephadex 50 (Pharmacia) cation-exchange chromatographic column, and the flow-through is collected. After buffer exchange in a PD-10 column (Pharmacia) to 0.02M sodium phosphate and 0.1M NaCl (pH 6.0), the solution is passed through a DEAE anion-exchange chromatographic column which is washed with 0.15M NaCl, 0.02M sodium phosphate buffer (pH 6.0). The column is eluted with a sodium chloride gradient from 0.15M to 0.5M.

The PDI-peptide complexes can be purified to apparent homogeneity using this procedure. About 3 to 7 μg of protein disulfide isomerase can be isolated from 1 g cells or tissue.

5.3. Determination of Immunogenicity of Stress Protein-Peptide Complexes

In an optional procedure, the purified stress protein-peptide complexes can be assayed for immunogenicity using the mixed lymphocyte target culture assay (MLTC) well known in the art.

By way of example but not limitation, the following procedure can be used. Briefly, mice are injected subcutaneously with the candidate stress protein-peptide complexes. Other mice are injected with either other stress protein-peptide complexes from normal, non-recombinant cells or whole infected cells which act as positive controls for the assay. The mice are injected twice, 7–10 days apart. Ten days after the last immunization, the spleens are removed and the lymphocytes released. The released lymphocytes may be restimulated subsequently in vitro by the addition of dead cells that expressed the complex of interest.

For example, $8 \times 10^6$ immune spleen cells may be stimulated with $4 \times 10^4$ mitomycin C treated or γ-irradiated (5–10,000 rads) infected cells (or cells transfected with an appropriate gene, as the case may be) in 3 ml RPMI medium containing 10% fetal calf serum. In certain cases 33% secondary mixed lymphocyte culture supernatant may be included in the culture medium as a source of T cell growth factors (See, Glasebrook et al., 1980, J. Exp. Med. 151:876). To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay (See, Palladino et al., 1987, Cancer Res. 47:5074–5079 and Blachere, at al., 1993, J. Immunotherapy 14:352–356). In this assay, the mixed lymphocyte culture is added to a target cell suspension to give different effector:target (E:T) ratios (usually 1:1 to 40:1). The target cells are prelabelled by incubating $1 \times 10^6$ target cells in culture medium containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5%.

5.4. Formulation

Noricovalent complexes of hsps and cancer proteins or peptides of the invention prepared by the claimed methods of the invention may be formulated into pharmaceutical preparations for administration to mammals for treatment or prevention of cancer. Drug solubility and the site of absorption are factors which should be considered when choosing the route of administration of a therapeutic agent. Hsp-antigenic molecule complexes of the invention may be administered using any desired route of administration, including but not limited to, e.g., subcutaneously, intravenously or intramuscularly, although intradermally or mucosally is preferred. Advantages of intradermal or mucosal administration include use of lower doses and rapid absorption, respectively. Mucosal routes of administration include, but are not limited to, oral, rectal and nasal administration. Preparations for mucosal administrations are suitable in various formulations as described below. The route of administration can be varied during a course of treatment. Preferred dosages, routes of administration and therapeutic regimens are described herein, and in PCT International patent applications published as WO 96/10411 and WO 97/10001, incorporated by reference herein in their entireties.

In preferred aspects, an amount of hsp70- and/or gp96-peptide complex is administered to a human that is in the range of about 10 to 600 $\mu$g, preferably 10 to 100 $\mu$g, most preferably about 25 $\mu$g, given once weekly for about 4–6 weeks, intradermally or mucosally with the site of administration varied sequentially. Preferred amounts for hsp90-peptide molecule complexes are in the range of 50 to 5,000 $\mu$g, preferably 100 $\mu$g.

Compositions comprising noncovalent complexes formulated in a compatible pharmaceutical carrier may be prepared, packaged, and labelled for treatment of the indicated tumor, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease, etc.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the noncovalent complexes and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the complexes. Such compositions may take the form of tablets or lozenges formulated in conventional manner.

For administration by inhalation, the complexes may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the complexes and a suitable powder base such as lactose or starch.

The complexes may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The complexes may also be formulated in rectal compositions such as suppositories or retention enemas, e.g., containing conventional suppository bases such as cocoa butter or other glycerides.

In addition to the formulations described previously, the complexes may also be formulated as a depot preparation. Such long acting formulations may be administered by implantation (for example, subcutaneously or intramuscularly) or by intramuscular injection. Thus, for example, the complexes may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the noncovalent complexes. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the noncovalent hsp-peptide complexes in pharmaceutically acceptable form. The hsp-peptide complexes in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of hsp-peptide complexes by a clinician or by the patient.

5.5. Prevention and Treatment of Cancer

There are many reasons why immunotherapy as provided by the noncovalent hsp-peptide complexes prepared by the present invention is desired for use in cancer patients. First, if cancer patients are immunosuppressed, and surgery with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

In a specific embodiment, the preventive and therapeutic utility of the invention is directed at enhancing the immunocompetence of the cancer patient either before surgery, at or after surgery, and at inducing tumor-specific immunity to cancer cells, with the objective being inhibition of cancer, and with the ultimate clinical objective being total cancer regression and eradication.

According to the invention, preferred methods of treatment or prevention of cancer comprise isolating RNA molecules from cancer cells obtained from one or more individual, preferably the individual in need of treatment, and making cDNA molecules from the RNA molecules isolated therefrom. The cancer cDNAs are manipulated by methods described above in section 5.1, such that the cDNA molecules, in the form of an expression construct, or intrachromosomally integrated, are suitable for expression of the cDNA molecules in one or more preselected host cells. The recombinant host cells containing the cDNA molecules are cultured under conditions such that peptides encoded by the cDNA molecules are expressed by the recombinant host cells. Complexes of heat shock protein noncovalently associated with one or more peptides are recovered and/or preferably purified from the recombinant host cells by the methods described in section 5.2. Depending on the route of administration, the hsp-peptide complexes are formulated accordingly as described in section 5.4, and administered to the individual autologously (e.g., to treat the primary cancer or metastases thereof), or to other individuals who are in need of treatment for cancer of a similar tissue type, or to individuals at enhanced risk of cancer due to familial history or environmental risk factors. Exemplary methods of therapeutic and prophylactic uses of hsp-peptide complexes have also been described in PCT Publications WO 96/10411, dated Apr. 11, 1996, and WO 97/10001, dated Mar. 20, 1997.

In one specific embodiment, the invention provides a method of treating or preventing cancer in an individual in whom treatment or prevention of cancer is desired comprising the steps of:

(a) culturing host cells containing cDNA molecules made from RNA molecules of cancer tissue obtained from one or more human individuals, under conditions such that proteins encoded by the cDNA molecules are expressed by the host cells;

(b) recovering from the host cells complexes of a heat shock protein noncovalently associated by one or more peptides, optionally purifying the recovered complexes; and (c) administering to the subject the recovered or purified complexes.

In another specific embodiment, the present invention provides a method of treating an individual having cancer comprising the following steps:

(a) isolating RNA molecules from cancer cells obtained from the individual;

(b) making cDNA molecules from the RNA molecules;

(c) introducing the cDNA molecules in a form suitable for expression of the cDNA molecules into one or more host cells;

(d) culturing the host cells containing the cDNA molecules under conditions such that proteins encoded by the cDNA molecules are expressed by the host cells;

(e) recovering from the host cells complexes of heat shock protein noncovalently associated with one or more peptides, optionally purifying the recovered complexes; and (f) administering to the individual the recovered or purified complexes.

Cancers that can be treated or prevented by using noncovalent hsp-peptide complexes prepared by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. Specific examples of such cancers are described in the sections below.

In a specific embodiment, the cancer is metastatic. In another specific embodiment, the patient having a cancer is immunosuppressed by reason of having undergone anticancer therapy (e.g., chemotherapy radiation) prior to administration of the hsp-peptide molecule complexes of the invention. In another specific embodiment, the cancer is a tumor.

The effect of immunotherapy with hsp-peptide complexes on progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in individuals at high risk, and f) changes in the morphology of tumors using a sonogram. Other techniques that can also be used include scintigraphy and endoscopy.

For example, to determine the activity of cytotoxic T cells in vitro, $8 \times 10^6$ peripheral blood derived T lymphocytes are isolated by the Ficoll-Hypaque centrifugation gradient technique. The cells are restimulated with $4 \times 10^4$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors. In order to measure the primary response of cytolytic T-lymphocytes after immunization, T cells are cultured without the stimulator tumor cells. In other experiments, T cells are restimulated with antigenically distinct cells. After six days, the cultures are tested for cytotoxity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of 12.5% (Heike et al., 1994, J. Immunotherapy 15:165–174).

An alternative to the chromium-release assay is the ELISPOT assay which measures cytokine release by cytotoxic T cells in vitro after stimulation with specific antigen. Cytokine release is detected by antibodies which are specific for a particular cytokine, such as interleukin-2, tumor necrosis factor α or interferon-γ (for example, see Scheibenbogen et al., 1997, Int. J. Cancer, 71:932–936). The assay is carried out in a microtitre plate which has been pre-coated with an antibody specific for a cytokine of interest which captures the cytokine secreted by T cells. After incubation of T cells for 24–48 hours in the coated wells, the cytotoxic T cells are removed and replaced with a second labelled antibody that recognizes a different epitope on the cytokine. After extensive washing to remove unbound antibody, an enzyme substrate which produces a colored reaction product is added to the plate. The number of cytokine-producing cells is counted under a microscope. This method has the advantages of short assay time, and sensitivity without the need of a large number of cytotoxic T cells.

By way of an example, the immune response in subjects after immuninization can be assessed by an IFN-γ ELISPOT assay kit (Mabtech, Sweden) as follows. Blood samples (20 ml) drawn from patients are heparinized, and peripheral blood mononuclear cells are separated from the blood samples by Ficoll (Pharmacia) gradient centrifugation. The separated blood cells may be stored in aliquots of $5 \times 10^6$ cells at $-130°$ C. CD8+ T cells are isolated from the blood cells by standard techniques, such as the use of magnetic beads (Dynal). HA-Multiscreen plates (Millipore) are coated with 100 μl of mouse-anti-human IFN-γ antibody (10 μg/ml). CD8+ T cells are plated at a concentration of $8 \times 10^4$ cells/well. Tumor cells ($5 \times 10^4$ cells/well) or tumor cell membranes ($5 \times 10^7$ cell equivalents/well) are added and incubated for 20 hours at 37° C. After the incubation, the cells are removed by extensive washing with PBS/0.05% Tween 20, and 100 μl of biotinylated capture-antibody against human IFN-γ are added at a concentration of 2 μg/ml. Spot development is performed by standard techniques and spots are counted using a stereomicroscope at a 40-fold magnification. Each spot corresponds to one CD8+ T cell secreting IFN-γ.

The preventive effect of immunotherapy using hsp-peptide complexes may also be estimated by determining levels of a putative biomarker for risk of a specific cancer. For example, in individuals at enhanced risk for prostate cancer, serum prostate-specific antigen (PSA) is measured by the procedure described by Brawer et al., 1992, J. Urol. 147:841–845, and Catalona et al., 1993, JAMA 270:948–958; or in individuals at risk for colorectal cancer, CEA is measured by methods known in the art; and in individuals at enhanced risk for breast cancer, 16-α-hydroxylation of estradiol is measured by the procedure described by Schneider et al., 1982, Proc. Natl. Acad. Sci. USA 79:3047–3051. The references cited above are incorporated by reference herein in their entirety.

6. EXAMPLE: TREATMENT OF HEPATOCELLULAR CARCINOMA

A liver biopsy sample (approximately $10^6$–$10^7$ cells, or 200 mg to 1 g of tissue) obtained from a patient with hepatocellular carcinoma is lysed gently in the presence of guanidinium isothiocyanate and phenol/chloroform. After centrifugation of the cell lysate, 1–2 mg of total RNA is extracted from about 1 g of tissue, and precipitated in isopropanol. Total poly-A$^+$ RNA is isolated from total RNA by column chromatography using commercially available prepacked oligo-dT cellulose spin columns (Clontech Laboratories, Calif.). Approximately 50 μg of poly-A$^+$ RNA is yielded from 1 mg of total RNA.

A commercial cDNA synthesis kit is used to make cDNA molecules from the poly-A$^+$ RNA with the approriate termini which is cloned unidirectionally into the BamHI/XbaI sites of the vector λDR2 (Clontech Laboratories, Calif.). This cloning vector contains an embedded version of the Epstein-Barr virus shuttle vector pDR2 which provides the elements for stable gene expression in permissive human cell lines. The 5' end of the cDNAs are inserted at the BamHI site which is downstream of the promoter of the Rous sarcoma virus long terminal repeat (RSV LTR) for expression in human cells.

The cloned cDNAs are packaged in vitro using commercially available E. coli cell extracts, and a portion of the packaged library is stored as λ phage particles. The other portion of the library is propagated by infecting E. coli AM1 strain host cells which contains the Cre recombinase. By site specific recombination via the loxP sites in the vector, the cloned cDNAs are converted into pDR2 plasmids carrying the expression constructs. The expression plasmids are purified from E. coli cells, and transfected into 293-EBNA cells (Invitrogen, Calif.), a human cell line constitutively expressing the neomycin resistance gene and the Epstein-Barr virus nuclear antigen which confers stable episomal maintenance of the expression plasmid. About 10–20 copies of the plasmid is maintained per cell and expression of the cloned cDNAs are driven by the RSV LTR promoter.

The transfected human cells are cultured in batches or continuously to allow recombinant production of the cloned cDNAs. Heat shock protein-peptide complexes are purifed from the recombinant cells as described in Section 5.2.

Treatment with hsp-antigen complexes prepared as described above is started any time after surgery. However, if the patient has received chemotherapy, hsp-antigen complexes are usually administered after an interval of four weeks or more so as to allow the immune system to recover. The immunocompetence of the patient is tested by procedures described in sections 5.9 above.

The therapeutic regimen includes weekly injections of the hsp-antigen complex, dissolved in saline or other physiologically compatible solution.

The dosage used for hsp70 or gp96 is in the range of 10 to 600 micrograms, with the preferred dosage for a human patient being 10 to 100 micrograms. The dosage used for hsp90 is in the range of 50 to 5,000 micrograms, with the preferred dosage for a human patient being 50 to 200 micrograms, e.g., 100 micrograms.

The route and site of injection is varied each time, for example, the first injection is given subcutaneously on the left arm, the second injection on the right arm, the third injection on the left abdominal region, the fourth injection on the right abdominal region, the fifth injection on the left thigh, the sixth injection on the right thigh, etc. The same site is repeated after a gap of one or more injections. In addition, injections are split and each half of the dose is administered at a different site on the same day.

Overall, the first four to six injections are given at weekly intervals. Subsequently, two injections are given at two-week intervals, followed by a regimen of injections at monthly intervals. The effect of hsp-antigen complexes therapy is monitored by measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; and e) changes in putative biomarkers of risk for a particular cancer in individuals at high risk.

Depending on the results obtained, the therapeutic regimen is developed to maintain and/or boost the immunological responses of the patient, with the ultimate goal of achieving tumor regression and complete eradication of cancer cells.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

At is claimed is:

1. A method for producing complexes of heat shock protein noncovalently bound to peptide comprising:
   (a) making cDNA molecules from RNA molecules of a cancer or preneoplastic cell;
   (b) ligating the cDNA molecules into an expression construct such that substantially each cDNA molecule is operably associated with at least one regulatory region that controls expression of the cDNA molecule, to form a library of expression constructs;
   (c) introducing the library into one or more host cells;
   (d) culturing the host cells containing the cDNA molecules under conditions such that proteins encoded by the cDNA molecules are expressed by the host cells; and
   (e) recovering from the host cells complexes of heat shock protein noncovalently associated with one or more peptides.

2. A method for producing complexes of heat shock protein noncovalently bound to peptide comprising:
   (a) introducing into one or more host cells cDNA molecules made from RNA molecules of cancer or preneoplastic cells, wherein each cDNA molecule is operably associated with at least one regulatory region that controls expression of the cDNA molecules in the host cells;
   (b) culturing the host cells containing the cDNA molecules under conditions such that proteins encoded by the cDNA molecules are expressed by the host cells; and
   (c) recovering from the host cells complexes of heat shock protein noncovalently associated with one or more peptides.

3. A method for producing complexes of heat shock protein noncovalently bound to peptide comprising:
   (a) culturing host cells containing cDNA molecules made from RNA molecules of a cancer or preneoplastic cell, under conditions such that proteins encoded by the cDNA molecules are expressed by the host cells; and
   (b) recovering from the host cells complexes of a heat shock protein of the host cell noncovalently associated with one or more peptides.

4. A method for producing complexes of heat shock protein noncovalently bound to peptide comprising:
   (a) isolating RNA molecules from cancer or preneoplastic cells obtained from a human individual;
   (b) making cDNA molecules from the RNA molecules;
   (c) introducing the cDNA molecules; in a form suitable for expression of the cDNA molecules into one or more host cells;
   (d) culturing the host cells containing the cDNA molecules under conditions such that proteins encoded by the cDNA molecules are expressed by the host cells; and
   (e) recovering from the host cells complexes of heat shock protein noncovalently associated with one or more peptides.

5. A method for producing complexes of heat shock protein noncovalently bound to a peptide comprising:
   (a) culturing host cells containing cDNA molecules made from RNA molecules of cancer tissue obtained from a human individual, under conditions such that proteins encoded by the cDNA molecules are expressed by the host cells; and (b) recovering from the host cells complexes of a heat shock protein of the host cell noncovalently associated with one or more peptides.

6. A method for producing complexes of heat shock protein noncovalently bound to peptide comprising:

(a) introducing cDNA molecules made from RNA molecules of cancer or preneoplastic cells into one or more host cells such that the cDNA molecules are expressible by the host cells;

(b) culturing the host cells containing the cDNA molecules under conditions such that proteins encoded by the cDNA molecules are expressed by the host cells; and (c) recovering from the host cells complexes of a heat shock protein of the host cell noncovalently associated with one or more peptides.

7. The method of claim 1 or 4 in which the RNA molecules are isolated from cancer cells of more than one human individual.

8. The method of claim 1 in which the host cells are human cells.

9. The method of claim 5 in which the host cells are human cells.

10. The method of claim 1 in which the RNA molecules are total polyA$^+$ RNA.

11. The method of claims 5 or 6 in which the RNA molecules are total polyA$^+$ RNA.

12. The method of claim 8 in which the RNA molecules are total polyA$^+$ RNA.

13. The method of claim 5 in which the cancer tissue is excised from a single human individual, the RNA molecules are total polyA$^+$ RNA, and the host cells are human host cells.

14. The method of claim 6 in which step (c) comprises purifying the complexes.

15. The method of claim 13 in which step (b) comprises purifying the complexes.

16. The method of claim 1, 2, 3 or 4 in which the RNA molecules are obtained from cancer cells of a tumor, a leukemia, or a cancer cell line.

17. The method of claim 1, 2, 3 or 4 in which the RNA molecules are obtained from preneoplastic cells.

18. The method of claim 1, 2, 3 or 4 in which the cancer cells are of a human cancer cell line.

19. The method of claim 1 or 3 in which the RNA molecules are obtained from a metastasis.

20. The method of claim 1, 3, 5, or 6 in which the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenström's macroglobulinemia, and heavy chain disease.

21. The method of claim 1, 3 or 4 in which the RNA molecules are messenger RNA molecules.

22. The method of claim 1 further comprising amplifying the cDNA molecules in between steps (a) and (b) or in between steps (b) and (c).

23. The method of claim 4 further comprising amplifying the cDNA molecules prior to step (c).

24. The method of claim 1 further comprising before step (c) the steps of freezing the cDNA library of step (b), and thawing the library.

25. The method of claim 1 further comprising before step (c) the steps of introducing the library into intermediate host cells, culturing the intermediate host cells to propagate the library, and isolating the library from the intermediate host cells.

26. The method of claim 1 in which the expression construct is a plasmid, a phage, a phagemid, a viral vector, or a cosmid.

27. The method of claim 26 in which the expression construct is a shuttle vector capable of replicating in different host cell species.

28. The method of claim 1 in which step (e) comprises purifying the complexes.

29. The method of claim 4 in which step (e) comprises purifying the complexes.

30. The method of claim 3 in which step (b) comprises purifying the complexes.

31. The method of claim 1 or 3 in which the host cells are bacteria, fungi, insect cells, or animal cells.

32. The method of claim 2, 3, 4, or 6 in which the host cells are human cells.

33. The method of claim 1 or 3 in which the host cells are *E. coli, S. cerevisiae, S. pombe, S. frugiperda,* COS cells, VERO cells, HeLa cells, Daudi cells, or CHO cells.

34. The method of claim 1, 2, 3, 4, 5, or 6 in which the heat shock protein is selected from the group consisting of hsp70, hsp90, gp96, protein disulfide isomerase and a combination of any one or more of the foregoing.

35. The method of claim 1 or 3 in which the heat shock protein is hsp70.

36. The method of claim 1 or 3 in which the heat shock protein is hsp90.

37. The method of claim 1 or 3 in which the heat shock protein is gp96.

38. The method of claim 1 or 3 in which the heat shock protein is protein disulfide isomerase.

39. The method of claim 1 or 3 in which the host cells further contain a nucleotide sequence encoding a heat shock protein or a fusion protein comprising a heat shock protein, in which the nucleotide sequence is operably associated with a non-native regulatory region such that the heat shock protein or the fusion protein is expressed by the host cells.

* * * * *